(12) United States Patent
Miyagawa

(10) Patent No.: US 12,391,716 B2
(45) Date of Patent: Aug. 19, 2025

(54) PROCESS OF PREPARING NUCLEIC ACID OLIGOMER

(71) Applicant: SUMITOMO CHEMICAL COMPANY, LIMITED, Chuo-ku (JP)

(72) Inventor: Takuya Miyagawa, Osaka (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 639 days.

(21) Appl. No.: 17/792,484

(22) PCT Filed: Jan. 29, 2021

(86) PCT No.: PCT/JP2021/003351
§ 371 (c)(1),
(2) Date: Jul. 13, 2022

(87) PCT Pub. No.: WO2021/153770
PCT Pub. Date: Aug. 5, 2021

(65) Prior Publication Data
US 2023/0095584 A1   Mar. 30, 2023

(30) Foreign Application Priority Data
Jan. 29, 2020   (JP) ................. 2020-012789

(51) Int. Cl.
C07H 1/00      (2006.01)
C07H 13/00     (2006.01)
C07H 21/02     (2006.01)

(52) U.S. Cl.
CPC ............ C07H 1/00 (2013.01); C07H 13/00 (2013.01); C07H 21/02 (2013.01)

(58) Field of Classification Search
None
See application file for complete search history.

(56) References Cited

U.S. PATENT DOCUMENTS

| | | |
|---|---|---|
| 2007/0282097 A1 | 12/2007 | Ohgi et al. |
| 2014/0206856 A1 | 7/2014 | Aoki et al. |
| 2022/0251128 A1 | 8/2022 | McPherson et al. |
| 2023/0312635 A1 | 10/2023 | Miyagawa et al. |

FOREIGN PATENT DOCUMENTS

| | | |
|---|---|---|
| CN | 115003682 A | 9/2022 |
| EP | 1 795 536 A1 | 6/2007 |
| EP | 2 749 565 A1 | 7/2014 |
| WO | WO 2018/212236 A1 | 11/2018 |
| WO | WO 2020/236618 A1 | 11/2020 |
| WO | WO 2020/249571 A1 | 12/2020 |

OTHER PUBLICATIONS

Combined Chinese Office Action and Search Report issued Jun. 28, 2024 in Chinese Application 202180011006.7, (with English translation), 9 pages.
International Search Report and Written Opinion issued May 14, 2021, in PCT/JP2021/003351, 9 pages.
Xia Wei, "Coupling activators for the oligonucleotide synthesis via phosphoramidite approach", Tetrahedron 2013, 69, pp. 3615-3637.

Primary Examiner — Patrick T Lewis
(74) Attorney, Agent, or Firm — Oblon, McClelland, Maier & Neustadt, L.L.P.

(57) ABSTRACT

The present invention provides an efficient process for preparing a nucleic acid oligomer, that is, a process for preparing a nucleic acid having a phosphate triester bond effectively by oxidizing a nucleic acid precursor having a phosphite triester bond. Specifically, the present invention provides a process for preparing a nucleic acid compound having at its 5'-terminus a nucleotide represented by formula (I) by a phosphoramidite method, which comprises a step of reacting a precursor having a phosphite triester bond represented by a formula (II) (the definitions of substituents of formulae (I) and (II) are described in the Description) with an oxidation solution subjected to a heat-treatment that contains iodine, pyridine and water.

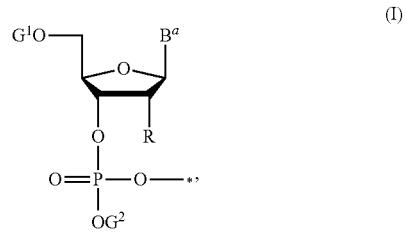

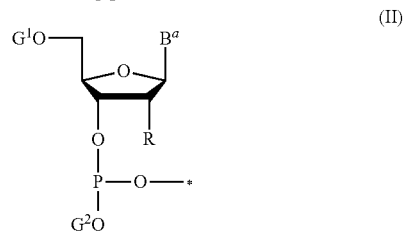

23 Claims, 1 Drawing Sheet
Specification includes a Sequence Listing.

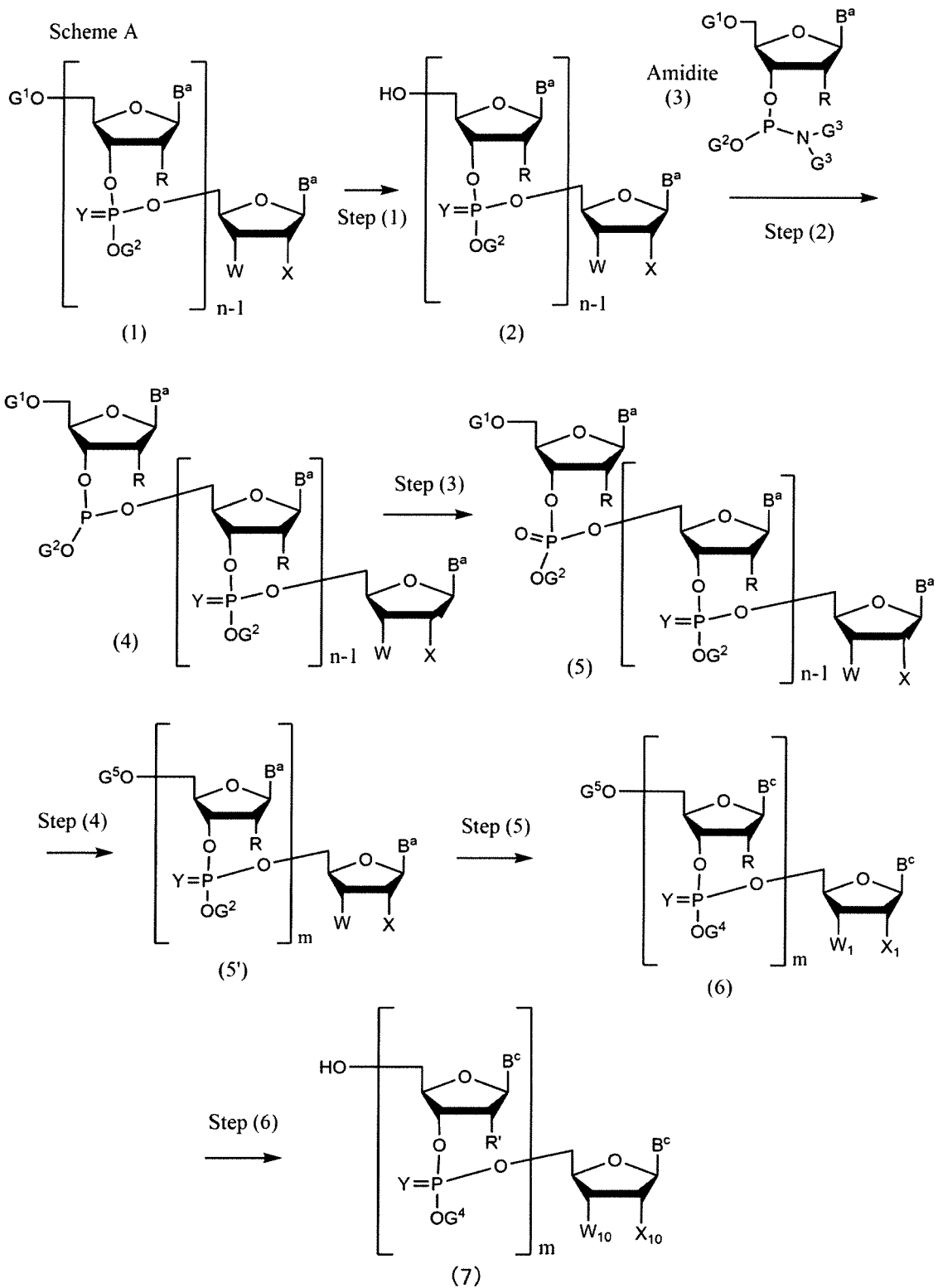

PROCESS OF PREPARING NUCLEIC ACID OLIGOMER

CROSS-REFERENCE TO RELATED APPLICATIONS

The present application is a 35 U.S.C. § 371 national stage patent application of International patent application PCT/JP2021/003351, filed on Jan. 29, 2021, which is based on and claims the benefits of priority to Japanese Application No. 2020-012789, filed on Jan. 29, 2020. The entire contents of these applications are incorporated herein by reference.

TECHNICAL FIELD

This application claims priority to and the benefit of Japanese Patent Application No. 2020-012789 filed Jan. 29, 2020, the entire contents of which are incorporated herein by reference.

The present invention relates to a process for preparing nucleic acid oligomer.

BACKGROUND ART

DNA and RNA which are a nucleic acid oligomer can be applied as a DNA probe, a RNA probe, an antisense, a ribozyme, a siRNA, or an aptamer and so on, which is a useful material.

A nucleic acid oligomer can be synthesized by a solid phase synthesis, and in the solid phase synthesis, a phosphoramidite of a nucleotide (hereinafter, referred to as "amidite") is used as a raw material. A nucleic acid oligomer that is synthesized by elongating a nucleic acid through a coupling step, an oxidation step and a deprotection step on a solid support is cut off from a solid support, and a protecting group is then removed to prepare a desired nucleic acid oligomer. However, the purity of the nucleic acid oligomer synthesized according to this method was not necessarily satisfactory, and the synthesis method was not thus efficient (see Non-Patent Literature 1).

CITATION LIST

Non Patent Literature

NPL 1: Tetrahedron 69 (2013) 3615-3637

SUMMARY OF INVENTION

Technical Problem

An object of the present invention is to provide an efficient process for preparing a nucleic acid oligomer.

Solution to Problem

The present inventors have intensively studied to achieve the above object, and as a result, can find out in a synthesis of nucleic acid oligomer, a heat-treated oxidation solution which contains iodine, water and pyridine is used as an oxidation solution in an oxidation of phosphite ester which is produced by a coupling reaction using phosphoramidite, thereby a nucleic acid oligomer can be prepared effectively. The present invention can provide an efficient process for preparing nucleic acid oligomer.

The present invention encompasses the following aspects, but are not limited thereto.

[1] A process for preparing a nucleic acid compound having at its 5'-terminus a nucleotide represented by formula (I):

[Chem. 1]

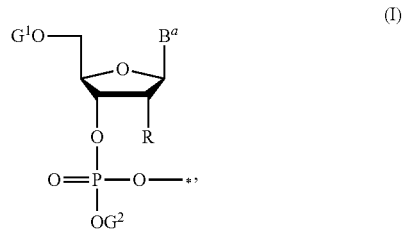

(I)

(wherein $G^1$ and $G^2$ each represents independently of each other a protecting group for hydroxy group, and $B^a$ represents a nucleic acid base which may be optionally protected with a protecting group, R represents a protected hydroxy group, a hydrogen atom, a fluorine atom, a methoxy group, a 2-methoxyethyl group, or a OQ' group, Q' represents a methylene group attached to a carbon atom at 4'-position of ribose, an ethylene group attached to a carbon atom at 4'-position of ribose, or an ethylidene group attached to a carbon atom at 4'-position of ribose, and a bond marked with symbol * represents a bond directing to 3' terminus side of a nucleic acid)

by a phosphoramidite method, which comprises a step of reacting a precursor having a phosphite triester bond rep resented by a formula (II):

[Chem.2]

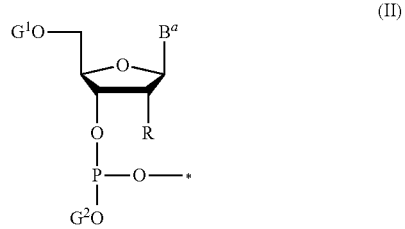

(II)

(wherein $G^1$, $G^2$, $B^a$, R and * are the same as defined above)

with an oxidation solution subjected to a heat-treatment at 40° C. or higher that contains iodine, pyridine and water (hereinafter, referred to as "Oxidation solution of the present invention").

[2] The process according to [1] wherein the precursor having a phosphite triester bond represents a nucleic acid compound represented by formula (4):

[Chem.3]

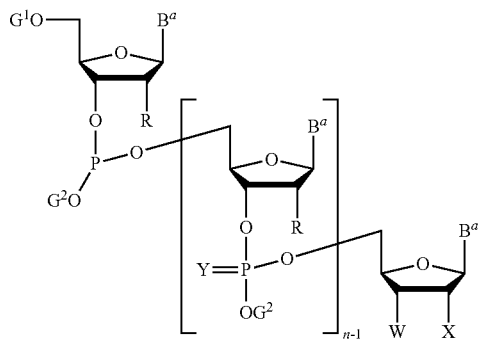

(wherein
$G^1$ represents a protecting group for hydroxy group,
$G^2$ is the same or different and each independently represents a protecting group for hydroxy group,
$B^a$ represents independently of each other the same or different nucleic acid base which may be protected with a protecting group,
R is the same or different and each independently represents a protected hydroxy group, a hydrogen atom, a fluorine atom, a methoxy group, a 2-methoxyethyl group, or OQ' group,
Q' is the same or different and each independently represents a methylene group attached to a carbon atom at 4'-position of ribose, an ethylene group attached to a carbon atom at 4'-position of ribose, or an ethylidene group attached to a carbon atom at 4'-position of ribose,
Y is the same or different and each independently represents an oxygen atom or a sulfur atom,
n is any integer of 1 or more to 200 or less,
when X represents OZ, W represents a OV group, and V represents a protecting group for hydroxy group,
when X represents a R group, W represents a group represented by OZ,
Z represents a group having a structure comprising a solid support and a connecting group, and
when n is an integer of 2 or more, the nucleic acid compound represented by formula (4) may be incorporated by a non-nucleotide linker instead of at least one nucleotide between nucleotides at 5' terminus and 3' terminus of the nucleic acid compound), the compound containing a phosphate triester bond represents a compound represented by formula (5):

[Chem.4]

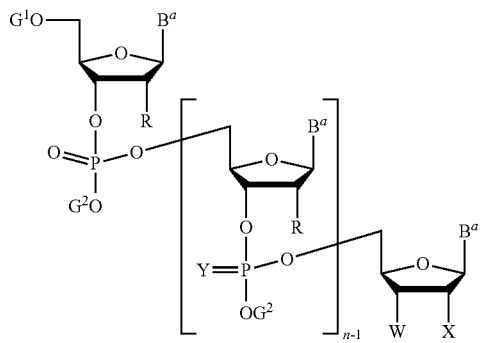

[wherein
$G^1$, $G^2$, $B^a$, R, n, W, X, and Y are the same as defined above, and as defined in formula (4), a non-nucleotide linker may be incorporated instead of a nucleotide)
[3] The process for preparing nucleic acid oligomer according to [2], which comprises
a step of elongating a chain strength of a nucleic acid compound represented by formula (5) to any chain length by an amidite method to obtain a nucleic acid repsented by formula (5'):

[Chem.5]

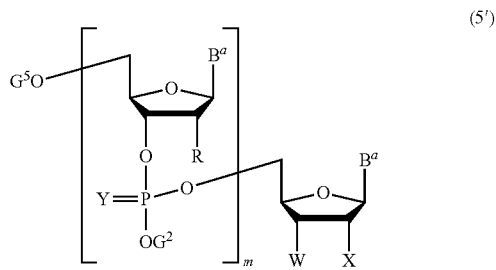

(wherein
$G^2$, $B^a$, R, X and W are the same as defied in formula (5),
$G^5$ represents a protecting group for hydroxy group, or a hydrogen atom,
m is an integer satisfying m≥n,
Y is the same or different and each independently represents an oxygen atom or a sulfur atom, with the proviso that at least one of Y is an oxygen atom), a step of cutting out the compound represented by formula (6):

[Chem.6]

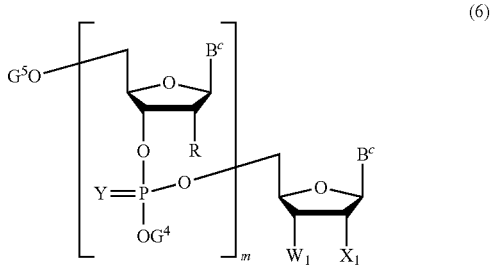

(wherein
$G^5$, R and m are the same as defined above,
$B^c$ is the same or different and each independently represents a nucleic acid base,
$G^4$ represents a hydrogen atom, an alkali metal ion, an ammonium ion, an alkyl ammonium ion, or a hydroxyalkyl ammonium ion,
Y represents independently of each other an oxygen atom or a sulfur atom, and at least one thereof is an oxygen atom, and
$X_1$ represents a hydroxy group, and $W_1$ represents a OV group wherein V represents a protecting group for hydroxy group, or
$X_1$ represents a R group and $W_1$ represents a hydroxy group) from the compound represented by formula (5'),
further a step of deprotecting the compound represented by formula (6) to prepare a deprotected nucleic acid oligomer represented by formula (7):

[Chem.7]

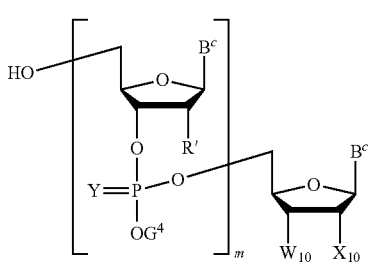
(7)

(wherein m, Y, $G^4$, and $B^c$ are the same as defined above,

R' is the same or different and each independently represents a hydroxy group, a hydrogen atom, a fluorine atom, a methoxy group, a 2-methoxyethyl group, or a OQ' group, Q' is the same or different and each independently represents a methylene group attached to a carbon atom at 4'-position of ribose, an ethylene group attached to a carbon atom at 4'-position of ribose, or an ethylidene group attached to a carbon atom at 4'-position of ribose, $X_{10}$ and $W_{10}$ each represents independently of each other a hydroxy group, or $X_{10}$ represents a R' group, and $W_{10}$ represents a hydroxy group).

[4] The process according to the above [2] or [3] wherein the non-nucleotide linker is a linker composed by an amino acid backbone.

[5] The process according to [4] wherein the linker comprising an amino acid backbone is a linker having a structure selected from the following formulae (A14-1), (A14-2) and (A14-3).

[Chem.8]

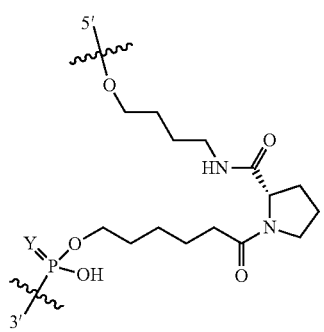
(A14-1)

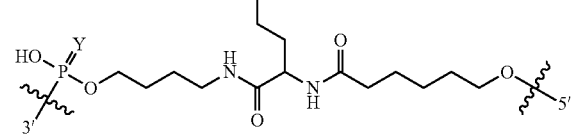
(A14-2)

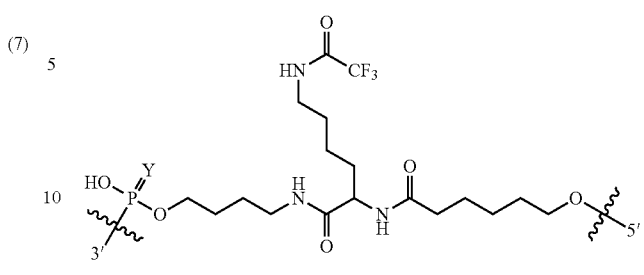
(A14-3)

[6] The process according to any one of [1] to [5] wherein a concentration of iodine in an oxidation solution is 0.005 to 2 M.

[7] The process according to any one of [1] to [5] wherein a concentration of iodine in an oxidation solution is 0.005 to 0.2 M.

[8] The process according to any one of [1] to [5] wherein a concentration of iodine in an oxidation solution is 0.007 to 0.1 M.

[9] The process according to any one of [1] to [5] wherein a concentration of iodine in an oxidation solution is 0.008 to 0.07 M.

[10] The process according to any one of [1] to [9] wherein the oxidation solution is prepared by mixing iodine, pyridine and water.

[11] The process according to [10] wherein the oxidation solution is an oxidation solution containing at least one solvent selected from a group consisting of acetonitrile and tetrahydrofuran.

[12] The process according to [10] or [11] wherein the oxidation solution is an oxidation solution further containing acetonitrile solvent.

[13] The process according to [11] wherein a solvent of the oxidation solution is a mixture of solvents which is obtained by mixing pyridine, water, acetonitrile, and tetrahydrofuran in a volume ratio of 1 to 90:1 to 50:0 to 90:0 to 90.

[14] The process according to [11] or [12] wherein a solvent of the oxidation solution is a mixture of solvents which is obtained by mixing pyridine, water and acetonitrile in a volume ratio of 1 to 90:1 to 50:0 to 90.

[15] The process according to any one of [1] to [14] wherein the prepared oxidation solution is aged in storage until its use in the oxidation reaction for nucleic acid synthesis within a range of 40° C. or higher to 60° C. or less.

[16] The process according to any one of [1] to [15] wherein the nucleic acid compound is a nucleic acid compound containing a ribonucleoside (RNA).

[17] The process according to any one of [2] to [16] wherein the nucleic acid is ribonucleoside (RNA), and its 2' protecting group is a protecting group represented by formula (12):

[Chem.9]

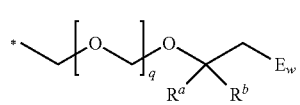
(12)

(wherein q is an integer of 1 to 5, $R^a$ and $R^b$ are the same or different and each independently represents a methyl group, an ethyl group, or a hydrogen atom, a bond marked with symbol * represents an oxygen atom of OQ group, and $E_w$ group represents an electron-attracting group).

[18] The process according to [17] wherein $R^a$ and $R^b$ are a hydrogen atom at the same time, and $E_w$ represents a cyano group.

[19] The process according to any one of [1] to [18] wherein the nucleic acid is a ribonucleoside (RNA) comprising 40 or more nucleotides in chain lengths.

[20] The process according to any one of [1] to [19], which further comprises a step of preparing an oxidation solution described in [1].

Effect of Invention

The present invention provides an effective process for preparing a nucleic acid oligomer. According to a process of the present invention, an improvement in a purity of a nucleic acid oligomer prepared can be expected.

BRIEF DESCRIPTION OF DRAWINGS

FIG. 1 is a figure showing a scheme of the steps (1) to (6) in the process of the present invention.

MODE FOR CARRYING OUT THE INVENTION

The following process is described: the process for preparing a nucleic acid compound having at its 5' terminus the nucleotide represented by the above formula (I), said process being a process for preparing a nucleic acid oligomer with high quality, by a phosphoramidite method, which comprises a step of reacting the precursor having a phosphite triester rep resented by the above formula (II) at a 5' terminus of the precursor with a heat-treated oxidation solution containing iodine, pyridine and water (referred to as "oxidation solution of the present invention").

The following process is described: the process for preparing a nucleic acid compound comprising a step of reacting a nucleic acid precursor having a phosphite triester bond with an oxidation solution containing iodine, pyridine and water, and thereby the phosphite triester bond is converted into a phosphate triester bond, wherein the above oxidation solution is the oxidation solution which is subjected to a heat-treatment.

Iodine can be used as an oxidizing agent, and the concentration (hereinafter, may be abbreviated as "conc.") of iodine in the oxidation solution containing iodine, pyridine and water is adjusted to a range of usually 0.005 to 2 M, preferably 0.005 to 0.2 M, more preferably 0.007 to 0.1 M, and further preferably 0.008 to 0.07 M.

The oxidation solution contains water and pyridine in addition to iodine, and examples of the solvent(s) that may be used include acetonitrile, tetrahydrofuran (THF), or a mixture of these solvents in an arbitrary ratio thereof, and preferred examples thereof include a mixture of pyridine and water, or a mixture of pyridine, water and acetonitrile.

The solution that can be used has a typical composition containing 1 to 90% by volume of pyridine, 1 to 50% by volume of water, and 0 to 90% by volume of acetonitrile, and 0 to 90% by volume of tetrahydrofuran to a total volume of the solution, which can be prepared by mixing the solvents at an arbitrary ratio to make a total volume of the solution 100% by volume, and include preferably a solvent wherein 5 to 90% by volume of pyridine, 2 to 30% by volume of water, 0 to 80% by volume of acetonitrile, and 0 to 80% by volume of tetrahydrofuran are mixed at an arbitrary ratio to make a total volume of the solution 100% by volume, and include more preferably a solvent wherein 90% by volume of pyridine and 10% by volume of water are mixed, or a solvent wherein 6% by volume of pyridine, 30% by volume of water, and 64% by volume of acetonitrile are mixed.

The stirring of the reaction system is not essential at preparing the oxidation solution, however usually the stirring is conducted within a range of 0.0 to 0.5 kW/m³ as the stirring power Pv, preferably 0.1 to 0.3 kW/m³.

A heat-treatment may be made to an oxidation solution having a higher iodine con centration than that of the oxidation solution finally used. In that case, the resulting oxidation solution is diluted with solvent(s) after storage and aging but before use to a finally adjusted concentration of iodine.

The oxidation solution to be used in the oxidation step in the process of the present invention is stored and aged at a temperature within a range of 20° C. or higher to 80° C. or less, preferably for example, 40° C. or higher to 60° C. or less, typically 60° C., before its use in the oxidation reaction in a nucleic acid synthesis. Also the period of the storage and aging of the solution is 1 hour or longer, preferably for example, within a range of 24 hours to 1 week, typically 24 hours.

For the storage of the oxidation solution in a container, a glass container, a plastic container or a metallic container can be used. Examples of the plastic container include a container made of polyethylene and polypropylene and so on, and examples of the metallic container include a SUS container, or a hastelloy container.

The oxidation solution can be stored under air atmosphere or inert gas atmosphere, and examples of the inert gas that may be used include argon, nitrogen, carbon dioxide, and helium.

Examples of the compounds that contain a phosphorous (phosphite) triester bond include the compound of formula (4) above. Examples of the nucleic acid compound resulting from with the reaction with the oxidation solution include the nucleic acid compound of formula (5).

In the formulae (4) and (5), examples of the compounds, wherein the Q' is the same or different and each independently represents a methylene group attached to a carbon atom at 4'-position of ribose, an ethylene group attached to a carbon atom at 4'-position of ribose, or an ethylidene group attached to a carbon atom at 4'-position of ribose, include the following structures of formula (8).

[Chem.10]

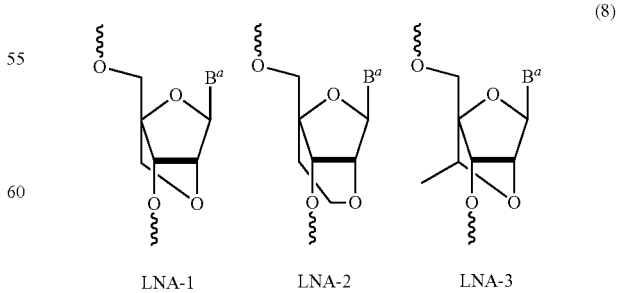

(8)

LNA-1    LNA-2    LNA-3

(wherein $B^a$ represents a nucleic acid base which may be optionally protected.)

Examples of the group represented by Z include, a group comprising a solid support, and a connecting moiety that connects the solid support and an oxygen atom of a hydroxy group at 2'-or 3'-position of a ribose at 3' terminus of the nucleic acid oligomer, and more specifically, Z represents a structure represented by formula (9):

[Chem. 11]

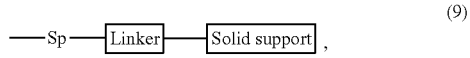
(9)

in the formula (9), Sp represents a spacer.

Examples of the spacer (Sp) include the structure represented by the following formula (10).

[Chem.12]

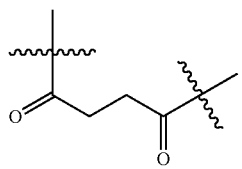
(10)

The Linker may for example, have a structure represented by the following formula (11), or a structure of the formula (11) wherein a hexamethylene amine moiety is not contained in the structure represented by the following formula (11) and thus the aminopropyl group is linked to Si, or the Linker may have a structure represented by the following formula (15).

[Chem.13]

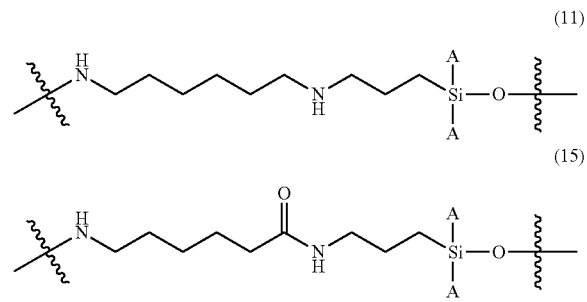

(wherein
A may be either a hydroxy group, an alkoxy group, or an alkyl group. Examples of the alkoxy group include a methoxy group, and an ethoxy group. Examples of the alkyl group include a methyl group, an ethyl group, an isopropyl group, a n-propyl group. Si represents that it binds to an oxygen atom of a hydroxy group on a support surface.)

Examples of the solid support include an inorganic porous support and organic resin support. Examples of the inorganic porous support include Controlled Pore Glass (CPG). Examples of the organic resin support include a support made of polystyrene.

Examples of the nucleoside (ribose and deoxyribose) contained in a nucleic acid oligomer to be used in the present invention include DNA, RNA, 2'-O-MOE (2-O-methoxymethyl), 2'-O-Me, 2'-F RNA, and the above LNA, and the above nucleoside is not limited thereto.

A synthesis method of nucleic acid oligomer comprising the oxidation step using the above oxidation solution by a solid phase synthesis comprises typically the following steps.

(1) a step of deprotecting the hydroxy group at 5'-position of a nucleoside having protected hydroxyl which is bound to a solid support via a linker, (2) a step of subjecting the resulting hydroxyl group at 5'-position in the previous step to a coupling reaction with a phosphoramidite compound to obtain a phosphite triester compound, (3) a step of preparing an elongated nucleic acid by oxidizing the phosphite triester produced in the previous step to a phosphate triester bond, or an optional step of converting the phosphite triester to a thiophosphate triester, (4) a step of preparing a nucleic acid on the solid support, comprising repeating optional number of the reaction cycle of steps (1) to (3), that is, the deprotection step of a hydroxy group at 5'-position of the resulting nucleic acid, a coupling step of the hydroxy group at 5'-position with an amidite compound, and an oxidation step of the produced phosphite triester, and (5) a step of cutting out the nucleic acid produced on the solid support in the above step (4), and then subjecting the resulting nucleic acid to a deprotection reaction, to liberate it from the solid support, and to prepare a deprotected nucleic acid oligomer, wherein in the synthesis method of the nucleic acid oligomer above, the step (2) or (3), may be followed by a step of capping a hydroxy group at 5'-position which has not proceeded with a coupling reaction with a phosphoramidite compound, or the capping step may be added between any steps of the reaction cycle in the step (4).

More specifically, the above step (5) is carried out by subjecting a nucleic acid molecule on a solid support which is produced in step (4) to the following reaction steps (5-1) and (5-2) in the order thereof, and then subjecting the resulting reaction products to the reaction step (5-3). Here the reaction step (5-1) may be optionally conducted, and the reaction step (5-2) may be conducted according to a method described in JP patent No. 4705716. As a result, a nucleic acid oligomer wherein a protecting group is removed from a nucleic acid molecule leaved from the solid support, or a nucleic acid oligomer wherein a hydroxy group is protected can be produced.

(5-1) a reaction of deprotecting a protecting group for hydroxy group at 5' terminus of a nucleic acid molecule, (5-2) a reaction of liberating the nucleic acid molecule by cutting out from a solid support, and (5-3) a reaction of deprotecting a protecting group for a hydroxy group at 2'-position of a ribose of a nucleic acid molecule or at 3'-position of a ribose located at 3' terminus.

The schemes of the above steps (1) to (6) are shown in FIG. 1. The oxidation reaction in the step (3) or the step (4) as depicted in FIG. 1 is carried out by using the above oxidation solution. The definition of the substituents contained in chemical formula in Scheme A is the same as defined above.

The nucleic acid compound of formula (5) can be further elongated to any chain length by using a nucleotide type or a non-nucleotide type of Linker according to an amidite method, and can be then used in a preparation of a nucleic acid compound represented by the above formula (5'). Also only a nucleic acid oligomer can be cut out from a nucleic acid compound which is bound to a solid support of the above formula (5') to obtain a nucleic acid oligomer represented by the above formula (6), and the resulting nucleic acid oligomer is then further deprotected to obtain a nucleic acid oligomer represented by the above formula (7).

Hereinafter, substituent in each formula is described in more detail.

A nucleic acid base which may be optionally protected with a protecting group represented by $B^a$ is not particularly limited. Examples of the nucleic acid base include adenine, cytosine, guanine, uracil, thymine, 5-methyl cytosine, pseudo uracil, 1-methyl pseudo uracil, and the others. Also the nucleic acid base may be optionally substituted with substituent(s). Examples of the substituent include a halogen atom (such as fluoro group, chloro group, bromo group, and iodo group), an acyl group (such as acetyl group), alkyl group (such as methyl group and ethyl group), arylalkyl group (such as benzyl group; alkoxy group (such as methoxyethyl group), cyanoalkyl group (such as cyanoethyl group), hydroxy group, acyloxymethyl group, amino group, monoalkylamino group, dialkylamino group, carboxy group, cyano group, and nitro group, as well as a combination of these two or more of the substituents.

In the case where a nucleic acid base contains an exocyclic amino group, the protecting group for the amino group is not particularly limited, and the protecting group used in a publicly known nucleic acid chemistry field may be used, and examples of the protecting group include benzoyl group, 4-methoxybenzoyl group, acetyl group, propionyl group, butyryl group, isobutyryl group, phenylacetyl group, phenoxyacetyl group, 4-tert-butylphenoxyacetyl group, 4-isopropylphenoxyacetyl group, and (dimethylamino)methylene group, as well as a combination of two or more of these protecting groups.

$B^a$ represents more specifically any groups indicated below.

[Chem. 14]

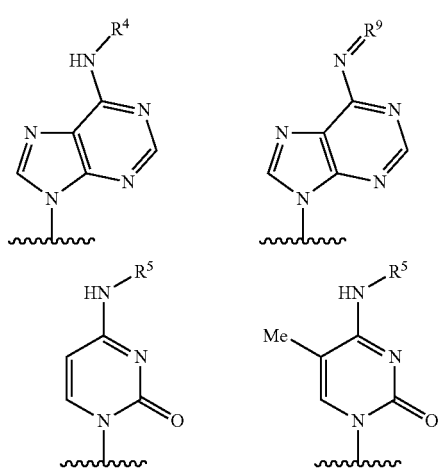

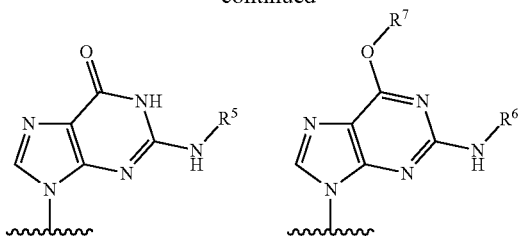

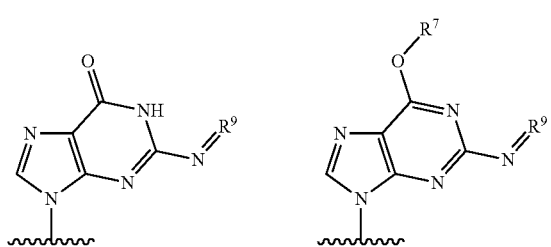

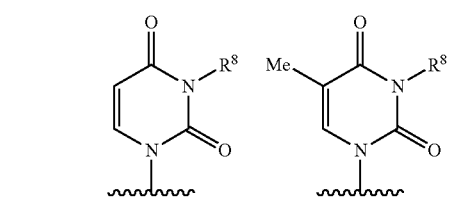

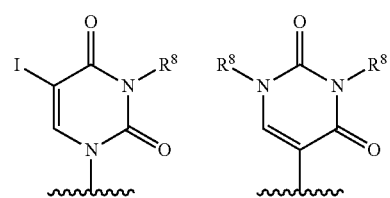

{wherein $R^4$ represents a hydrogen atom, a methyl group, a phenoxyacetyl group, a 4-tert-butylphenoxyacetyl group, a 4-isopropylphenoxyacetyl group, a phenylacetyl group, an acetyl group, or a benzoyl group, $R^5$ represents a hydrogen atom, an acetyl group, an isobutyryl group, or a benzoyl group, $R^6$ represents a hydrogen atom, a phenoxyacetyl group, a 4-tert-butylphenoxyacetyl group, a 4-isopropylphenoxyacetyl group, a phenylacetyl group, an acetyl group or an isobutyryl group, $R^7$ represents a 2-cyanoethyl group, $R^8$ represents a hydrogen atom, a methyl group, a benzoyl group, a 4-methoxybenzoyl group, or a 4-methylbenzoyl group, and $R^9$ represents a dimethylaminomethylene group.)

$G^1$ can be used without any particularly limitation as long as it can function as a protecting group, and a publicly known protecting group used for the amidite compound can be used widely G¹ represents preferably the following groups.

[Chem.15]

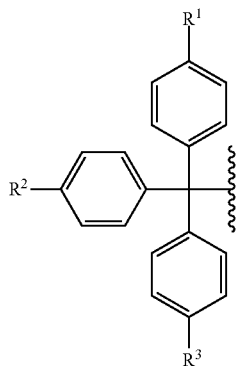

(wherein $R^1$, $R^2$ and $R^3$ are the same or different and each independently represents a hydrogen atom or an alkoxy group.)

One of $R^1$, $R^2$ and $R^3$ represents a hydrogen atom, and the remaining two thereof are the same or different (preferably the same) alkoxy group, and as an alkoxy group, a methoxy group is particularly preferred.

G2 can be used without any particular limitation as long as it can function as a protecting group, and a publicly known protecting group for an amidite compound can be widely used. Examples of $G^2$ include an alkyl group, an alkenyl group, an alkynyl group, a cycloalkyl group, a haloalkyl group, an aryl group, a heteroaryl group, an arylalkyl group, a cycloalkenyl alkyl group, a cycloalkylalkyl group, a cyclylalkyl group, a hydroxyalkyl group, an aminoalkyl group, an alkoxyalkyl group, a heterocyclylalkenyl group, a heterocyclylalkyl group, a heteroarylalkyl group, a silyl group, a silyloxyalkyl group, a mono, di or tri-alkylsilyl group, a mono, di or tri-alkylsilyloxyalkyl group, and the others, and these groups may be optionally substituted with one or more electron-attracting group.

G2 represents preferably an alkyl group substituted with electron-attracting group. Examples of the electron-attracting group include a cyano group, a nitro group, an alkylsulfonyl group, a halogen atom, an arylsulfonyl group, a trihalomethyl group, a trialkylamino group, and the others, and preferably a cyano group.

Particularly preferable example of $G^2$ include the following groups.

[Chem.16]

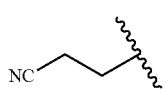

For $G^3$, two $G^3$ may be combined with each other to form a cyclic structure. Preferably, both $G^3$ are an isopropyl group.

The alkyl group as the definitions of the above $R^1$, $R^2$, $R^3$ and $G^2$ may be a straight chain group or a branched chain, and preferably include an alkyl group containing 1 to 12 carbon atoms, and more preferably an alkyl group containing 1 to 6 carbon atoms. Specific examples of alkyl group include a methyl group, an ethyl group, a n-propyl group, an isopropyl group, a n-butyl group, an isobutyl group, a tert-butyl group, a n-pentyl group, an isopentyl group, and a hexyl group. An alkyl group part composed of the alkoxy group in the definition for above substituents has the same definition as that described in the definition of alkyl group described here.

Also, in the process of the present invention, an amidite compound can be used in a free state or a salt state thereof. Examples of salts of the amidite compound include a base addition salt or an acid addition salt, which are not particularly limited thereto. Examples of the base addition salt include salts with inorganic bases such as sodium, magnesium, potassium, calcium, aluminium and the others; salts with organic base such as methylamine, ethylamine, ethanolamine and the others; salts with basic amino acids such as lysine, ornithine, arginine, and the others); and ammonium salt. Specific examples of acid addition salts include mineral acids such as hydrochloric acid, hydrobromic acid, hydroiodic acid, sulfuric acid, nitric acid, phosphoric acid, and the others); acid addition salts, for example, salts with organic acids such as formic acid, acetic acid, propionic acid, oxalic acid, malonic acid, maleic acid, tartaric acid, fumaric acid, succinic acid, lactic acid, maleic acid, citric acid, methanesulfonic acid, trifluoromethansulfonic acid, ethanesulfonic acid, and the others, and salts with acidic amino acids such as aspartic acid, glutamic acid, and the others. Examples of the amidite compounds encompass salts, hydrates, solvates, crystal polymorphs, and the others.

When R represents a protected hydroxy group, its protecting group may be any one which can be used in an amidite method, and for example, the followings can be used: those described in WO 2013/027843 A1 and WO 2019/208571 A1, in addition to 2'-tert-butyl dimethylsilyl (TBDMS) group, 2'-bis(2-acetoxy)methyl (ACE) group, 2'-(triisopropylsilyloxy)methyl (TOM) group, 2'-(2-cyanoethoxy)ethyl (CEE) group, 2'-(2-cyanoethoxy)methyl (CEM) group, 2'-para-toluylsulfonylethoxymethyl (TEM) group, 2'-EMM group (WO 2006/022323 A1). Among 2' protecting group of these ribonucleoside (RNA), the above-mentioned protecting group represented by formula (12) is exemplified as a preferable protecting group. Further preferably, as the electron-attracting group represented by $E_w$, a protecting group containing a cyano group represented by formula (13) is exemplified.

[Chem.17]

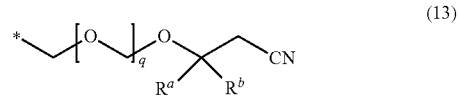

(13)

(wherein q, $R^a$ and $R^b$ are the same as defined above, with the proviso that $R^a$ and $R^b$ do not represent a hydrogen atom at the same time.)

The protecting group represented by formula (13) can be synthesized, for example, according to a method described in WO 2013/027843 A1 and WO 2019/208571 A1, and the amidite compound having such a protecting group can be used in a preparation of a nucleic acid compound.

For an elongation reaction of nucleic acid, the amidite compound of formula (3) a shown in Scheme A of FIG. 1 is used.

As non-nucleotide linker, a linker composed by amino acid backbone (for example, a linker composed by amino acid backbone as described in JP 5157168 B2 or JP 5554881 B2) is exemplified. Specifically, as a non-limiting example, a linker rep resented by formula (A14-1), formula (A14-2) or formula (A14-3) is exemplified. In addition to these linkers, a particular linker as described in WO 2012/005368 A1, WO 2018/182008 or WO 2019/074110 is exemplified.

[Chem.18]

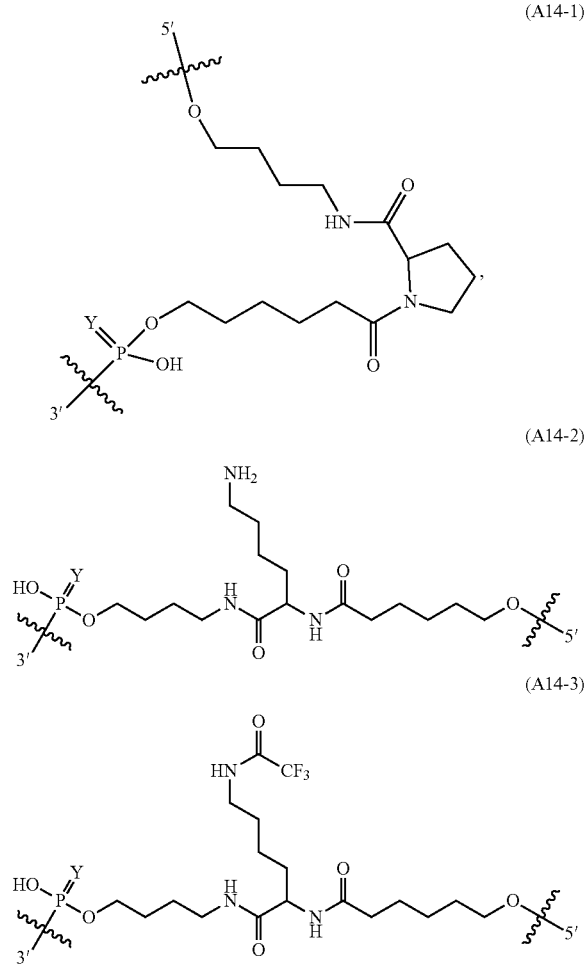

A nucleotide and an amidite wherein a R group in formula (3) and a R' group in formula (4) can be also prepared from nucleosides which are synthesized according to publicly known methods described in JP 3745226 B2 and so on, or WO 2001/053528 B2, JP 2014-221817 A1 or publicly methods referred to in these documents. Further, they can prepared by using a commercially available compound in line with the method described in the below Examples or methods with appropriate modifications to these methods.

For a synthesis of nucleic acid according to the amidite method in the above-mentioned steps (1) to (6), an elongation reaction of nucleic acid can be carried out by repeating each step such as a deprotection step and a condensation step, except for the oxidation step relating to the present invention in the step (3) in the scheme of FIG. 1 according to a generally known method (for example, the method described in the above JP 5157168 B2 or JP 5554881 B2). Hereinafter, each step is described.

$G^4$ represents a hydrogen atom, an alkali metal ion, ammonium ion, an alkyl ammonium ion, or a hydroxyalkylammonium ion. Examples of the alkali metal ion include a sodium ion, and a lithium ion. Also specific examples of alkyl groups include methyl, ethyl, n-propyl, isopropyl, n-butyl, isobutyl, tert-butyl, n-pentyl, isopentyl, and hexyl, and specific examples thereof include ammonium ion, diethyl ammonium ion, triethylammonium ion, tetrabutylammonium ion, hexylammonium ion, dibutyl ammonium ion, and the others. Also as hydroxy alkylammonium ion, specific examples of hydroxyalkyl part thereof include hydroxymethyl, hydroxyethyl, hydroxy n-propyl, hydroxy isopropyl, hydroxy n-butyl, and tris hydroxy methyl, and more specific examples of hydroxyalkyl ammonium include tris hydroxymethyl ammonium ion and the others.

$G^5$ represents a hydrogen atom or a protecting group, and when it represents a protecting group, it is the same as defined in $G^1$. When $G^5$ is deprotected, it is a hydrogen atom, and the nucleotide compound in the case is also provided in a series of steps for nucleic acid elongation reaction.

(Nucleic Acid Elongation Reaction)

As used herein, "nucleic acid elongation reaction" means that a reaction for elongating oligonucleotide by attaching nucleotide sequentially through phosphodiester bond. The nucleic acid elongation reaction can be carried out according to the procedures of general phosphoramidite method. The nucleic acid elongation reaction may be carried out with a nucleic acid automatic synthesizer and so on which applies a phosphoramidite method.

The chain length of a nucleic acid oligomer may be, for example, 2 to 200 mer, and 10 to 150 mer, and 15 to 110 mer.

A 5' deprotection step in the step (1) is a step where a protecting group of a 5' hydroxyl group at RNA chain terminus which is supported on the solid support. As a general protecting group, 4,4'-dimethoxytrityl group (DMTr group), 4-monomethoxytrityl group, and 4,4',4"-trimethoxy trityl group are used. A deprotection reaction can be carried out by using an acid. Examples of the acid for deprotection reaction include trifluoroacetic acid, dichloroacetic acid, trifluoroethansulfonic acid, trichloroacetic acid, methansulfonic acid, trifluoromethansulfonic acid, trichloroacetic acid, methansulfonic acid, hydrochloric acid, acetic acid, p-toluenesulfinic acid, and the others.

The condensation step in the step (2) is a reaction where a nucleoside phosphoramidite represented by the following formula (3) as described in Scheme A of FIG. 1 is attached to a 5' hydroxyl group at oligonucleotide chain terminus deprotected by the above deprotection step. As the phosphoramidite to be used in the nucleic acid elongation, an amidite compound represented by formula (3) or formula (A12) is used. Also, as another available phosphoramidite, 2'-OMe, 2'-F, 2'-o-tert-butyldimethyl silyl group, 2'-O-methoxyethyl group, 2'-H, 2'-fluoro-2'-deoxy-β-D-arabinofuranosyl and the others are included. As the above nucleoside phosphoramidite, those where 5' hydroxyl group is protected with a protecting group (for example, DMTr group) are used. The condensation step can be carried out by using an activator which activates the above-mentioned nucleotide phosphoramidite. Examples of the activator include 5-benzylthio-1H-tetrazole (BTT), 1H-tetrazole, 4,5-dicyanoimidazole (DCI), 5-ethylthio-1H-tetrazole (ETT), N-methyl benzimidazoliumtriflate (N-MeBIT), benzimidazoliumtriflate (BIT), N-phenylimidazoliumtriflate (N-PhIMT), imidazoliumtriflate (IMT), 5-nitrobenzimidazoliumtriflate (NBT), 1-hydroxybenzotriazole (HOBT), and 5-(bis-3,5-trifluoromethylphenyl)-1H-tetrazole, and the others.

The nucleotide phosphoramidite represented by formula (3) as described in Scheme A of FIG. 1 (hereinafter, referred to as "amidite") is shown below.

A compound represented by formula:

[Chem.19]

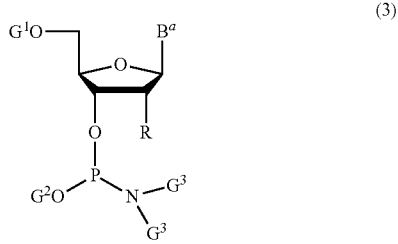

(3)

{wherein
$G^1$, $G^2$, $G^3$, $B^a$, and R are the same as defined above).

After the condensation step, as needed, the unreacted 5' hydroxyl group may be capped. The capping reaction can be carried out by using publicly known capping solution such as acetic anhydride-tetrahydrofuran solution, and phenoxy acetic anhydride/N-methyl imidazole solution.

The oxidation step of step (3) is a step for converting a phosphite group which is formed by the above condensation step into a phosphate group or a thiophosphate group. This step is a reaction of converting a trivalent phosphorus into pentavalent phosphorus using an oxidative agent, which can be carried out by acting an oxidation agent to oligonucleic acid derivatives supported on a solid support.

When a phosphite group is converted into a phosphate group, as "oxidation agent", for example, an iodine can be used. The oxidation agent can be used by adjusting a concentration thereof to 0.005 to 2 M. Water can be used as a oxygen source for oxidation, and pyridine and the others can be used as a base for proceeding with the reaction. Also the solvents are not particularly limited as long as they do not involve the reaction, and can be used as acetonitrile, tetrahydrofuran (THF) or a mixed solvents of these solvents at arbitrarily ratio. For example, iodine/water/pyridine/acetonitrile, or iodine/water/pyridine, or iodine/water/pyridine/THF can be used. The reaction temperature is preferably 5° C. to 50° C. The reaction period of the reaction is usually appropriate to be 1 min. to 30 min. The amount of the reagent used is within a range of 1 to 100 mole(s), preferably 1 to 10 mole(s), as opposed to 1 mole of the compound supported on as solid support.

When a phosphite triester group is converted into a thiophosphate group, as "oxidation agent", for example, a sulfur, 3H-1,2-benzodithiol-3-one-1,1-dioxide (Beaucage reagent), 3-amino-1,2,4-dithiazole-5-thione (ADTT), 5-phenyl-3H-1,2,4-dithiazole-3-one (POS), [(N,N-dimethylaminomethyline)amino]-3H-1,2,4-dithiazoline-3-thione (DDTT), and phenylacetyldisulfide (PADS) can be also used. The oxidation agent can be used by diluting it with an appropriate solvent so as to adjust to 0.001 to 2 M. The solvents to be used are not particularly limited as long as they do not involve the reaction, and include, for example, dichloromethane, acetonitrile, pyridine, or any mixed solvents of these solvents. The oxidation step may be carried out after the above mentioned capping procedure, or vice versa, the capping procedure may be carried after the oxidation step, and the order of the procedures are not limited.

Among the step (5), in the step of deprotecting a protecting group for a phosphorus group, when a synthesis of a nucleic acid having a desirable sequence is completed, an amine compound is acted to deprotect a protecting group of a phosphorus part. Examples of the amine compound include, for example, diethylamine and the others as described in JP 4705716 B2.

The protecting group for 5' hydroxyl group of a nucleoside introduced in the last stage of an elongation may be used for a column purification with 5' protecting group as a tag after the below-mentioned procedures of a cutting out from a solid support and a deprotection of a protecting group, or the protecting group for 5' hydroxyl group may be deprotected after the column purification.

In the step (5), the cutting out of a nucleic acid oligomer which is elongated to a desirable chain on a solid support from a solid support is usually carried out by using a concentrated ammonium water as a cutting out agent.

Further, using ammonia or amine compound or the others, for example, an oligo nucleotide chain is recovered by cutting it out from a solid support. Examples of the amine compound include methylamine, ethylamine, isopropylamine, ethylenediamine, diethylamine, and the others.

In the step (6), a protecting group for hydroxy group at 2 position or 3 position of ribose of the nucleic acid compound (6) which is cut out from a solid support in the step (5) can be removed according to a method described in WO 2006/022323 A1, WO 2013/027843 A1, or WO 2019/208571 A1 to obtain a deprotected nucleic acid oligomer (7).

Examples of the nucleic acid oligomer which can be prepared according to the process of the present invention include those wherein a nucleoside contained in the nucleic acid oligomer is RNA, DNA, as well as RNA having 2'-O-MOE, 2'-O-Me, 2'-F, and LNA, which is not limited thereto. For example, various nucleosides described in Xiulong, Shen et al., Nucleic Acids Research, 2018, Vol. 46, No. 46, 1584-1600, and Daniel O'Reilly et al., Nucleic Acids Research, 2019, Vol. 47, No. 2, 546-558 are included.

As typical examples of nucleic acid oligomer which can be used in the process of the present invention, the following examples are indicated in addition to examples described in working examples, which are not limited thereto.

Hereinafter, in a description of a sequence, u is uridine, c is cytidine, A is adenosine, or G is guanosine.

A nucleic acid oligomer having the following sequences (B) and (C) as described in WO 2019/060442 is exemplified.

```
Sequence (B):
                                    (Sequence No. 3)
5'-AUGGAAUmACUCUUGGUUmACdTdT-3'
(Antisense) 21 mer Sequence (C):
                                    (Sequence No. 4)
5'-GUmAACmCmAAGAGUmAUmUmCmCmAUmdTdT-3'
(Sense) 21 mer
```

In the sequence (B) and sequence (C), Um is 2'-O-methyluridine, Cm is 2'-o-methylcytidine, or dt is thymidine.

A nucleic acid oligomer as described in Daniel O'Reilly et al., Nucleic Acids Research, 2019, Vol. 47, No. 2, 546-558 is exemplified. Typical examples thereof include a nucleic acid oligomer having the following sequence (D).

Sequence (D):
(Sequence No. 5)
5'-AGAGCCAGCCUUCUUAUUGUUUUAGAGCUAUGCUGU-3'
36 mer A nucleic acid oligomer as described in JP 4965745 B2 is exemplified. Typical examples thereof include a nucleic acid oligomer having the following sequence (E).

Sequence(E):
5'-CCAUGAGAAGUAUGACAACAGCC-P-GGCUG

UUGUCAUACUUCUCAUGGUU-3'
49 mer.

(Sequence No. 6)
CCAUGAGAAGUAUGACAACAGCC, (Sequence No. 7)
GGCUGU-UGUCAUACUUCUCAUGGUU.

In the Sequence (E), "P" is depicted by a partial structure separated by wavy lines in the following formula (A5).

A nucleic acid oligomer having the following sequence (F) as described in Nucleic Acids Research, 2019, Vol. 47, No. 2:547 is exemplified.

Sequence (F):
(Sequence No. 8)
5'-ACAGCAUAGCAAGUUAAAAUAAGGCUAGUCCGUUA

UCAACUUGAAAAAGUGGCACCGAGUCGGUGCU-3'
67 mer

A nucleic acid oligomer having the following sequence (G) as described in JP 2015-523856, 173 is exemplified.

Sequence(E):
(Sequence No. 9)
5'-GUUUUCCCUUUUCAAAGAAAUCUCCUGGGCACCUAUC

UUCUUAGGUGCCCUCCCUUGUUUAAACCUGACCAGUUAAC

CGGCUGGUUAGGUUUUU-3'
94 mer

A nucleic acid oligomer as described in JP 2017-537626 is exemplified. Typical examples thereof include a nucleic acid oligomer having the following sequences (F), (G), (H), and (J).

Sequence (F):
(Sequence No. 10)
5'-AGUCCUCAUCUCCCUCAAGCGUUUUAGAGCUAGUAAU

AGCAAGUUAAAAUAAGGCUAGUCCGUUAUCAACUUGAAAA

AGUGGCACCGAGUCGGUGCUUUU-3'
100 mer

Sequence (G):
(Sequence No. 11)
5'-GCAGAUGUAGUGUUUCCACAGUUUAAGAGCUAUGCUG

GAAACAGCAUAGCAAGUUUAAAUAAGGCUAGUCCGUUAUC

AACUUGAAAAAGUGGCACCGAGUCGGUGCUUUUUUU-3'
113 mer

Sequence (H):
(Sequence No. 12)
5'-dAdGdTdCdCdTdCdAdTdCdTdCdCdCdTdCdA dAdGdCGUUUAAGAGCUAUGCUGGUAACAGCAUAGCA

AGUUUAAAUAAGGCUAGUCCGUUAUCAACUUGAAAAA

GUGGCACCGAGUCGGUGCUUUUUUU-3'
113 mer in the sequence (H),
dt is thymidine,
de is 2'-deoxycytidine,
dA is 2'-deoxyadenosine,
or dG is 2'-deoxyguanosine.

Sequence (J):
(Sequence 13)
5'-AmsGmsUmsCCUCAUCUCCCUCAAGCGUUUAAG

AGCUAUGCUGGUAACAGCAUAGCAAGUUUAAAUAAG

GCUAGUCCGUUAUCAACUUGAAAAAGUGGCACCGA

GUCGGUGCUUUUmsUmsUmsU-3'
113 mer

In the Sequence (J), Um is 2'-O-methyluridine, Cm is 2'-O-methylcytidine, Am is 2'-O-methyladenosine, Gm is 2'-O-methylguanosine, or s is phosphorothioate modification.

EXAMPLES

Hereinafter, the resent invention is explained in more detail by working examples, and the present invention is not limited to these examples.

<Measurement Method>

Firstly, various measurement methods used in the following tests are shown below.

A purity of oligonucleotide was measured by HPLC.

A HPLC measurement condition is shown in the below Table 1.

(Measurement Method 1: Measurement of Oligonucleotide Purity)

TABLE 1

| Column | ACQUITY UPLC Oligonucleotide BEH C18, 2.1 mm × 100 mm, 1.7 μm × two columns |
|---|---|
| Flow rate | 0.2 mL/min |
| Detection wavelength | 260 nm |
| Mobile phase A | 100 mM aqueous hexylamine acetate (pH = 7.0) |
| Mobile phase B | 500 mM aqueous hexylamine acetate:acetonitrile = 1:4(v) |
| Gradient condition | Bconc. 43% (0 min) –56% (30 min) –90% (30.01 min) –90% (35 min) –43% (35.01 min) –43%(50 min) |
| Column temperature | 80° C. |

(Measurement Method 2: Measurement of Oligonucleotide Yield)

OD260 of the above crude product was measured. OD260 represents an absorbance at UV260 nm per 10 mm optical path length in a 1 mL solution (pH=7.5). Since it is generally known that 1 OD=40 μg for RNA, the yield was calculated based on the above measured value of OD260.

<Solid Phase Synthesis of Oligonucleotide>

[Chem. 22]

```
Sequence (1):
                           (Sequence Nos. 1, 2)
5'-AGCAGAGUACACACAGCAUAUACC-P-GGUAUA UGCUGUGUGUACUCUGCUUC-P-G-3'
3 mer
```

In the above sequence (I), "A" is represented by a partial structure separated by wavy lines in the following formula (A1). "C" is represented by a partial structure separated by wavy lines in the following formula (A2). "G" is represented by a partial structure separated by wavy lines in the following formula (A3). "U" is represented by a partial structure separated by wavy lines in the following formula (A4). "P" is represented by a partial structure separated by wavy lines in the following formula (A5). Here "A" at a 5' terminus is represented by a partial structure separated by wavy lines in the following formula (A6). Also "G" at a 3' terminus is represented by a partial structure separated by wavy lines in the following formula (A7).

```
                              (Sequence No. 1)
     AGCAGAGUAC ACACAGCAUA UACC (Sequence No. 2)
     GGUAUAUGCU GUGUGUACUC UGCUUC
```

[Chem. 20]

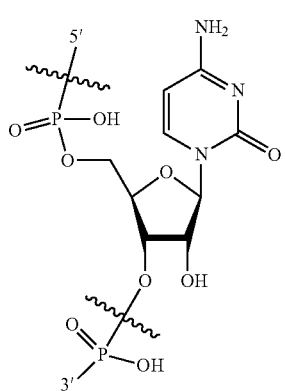

(A1)

[Chem. 21]

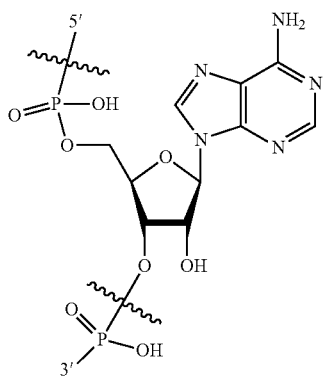

(A2)

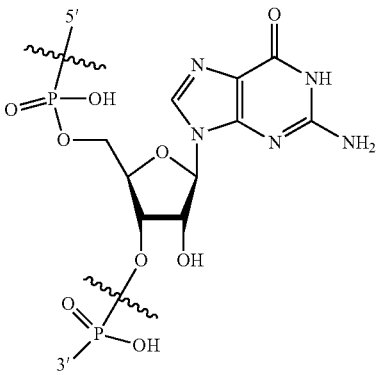

(A3)

[Chem. 23]

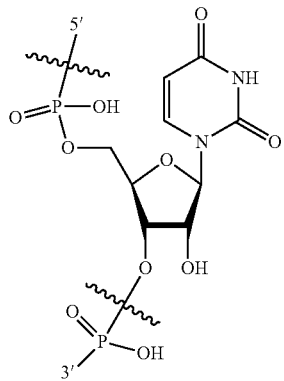

(A4)

[Chem. 24]

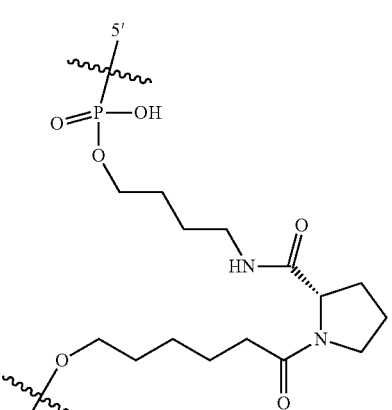

(A5)

[Chem. 25]

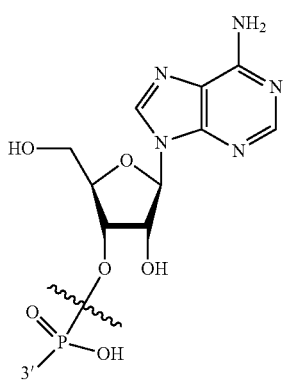

(A6)

[Chem. 26]

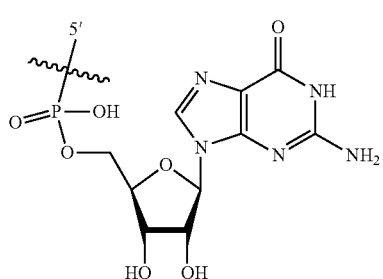

(A7)

[Chem. 27]

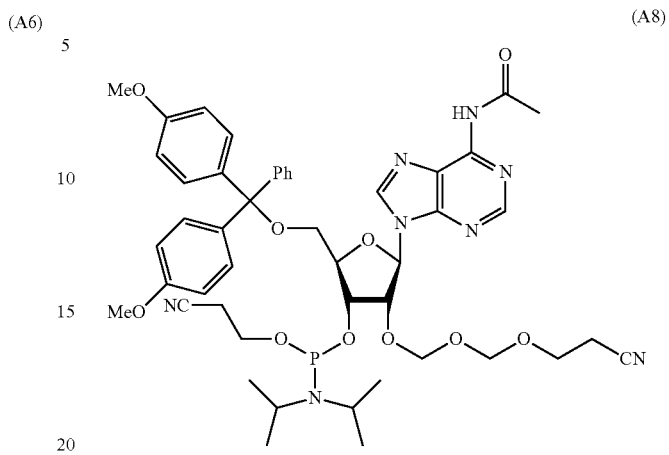

(A8)

[Chem. 28]

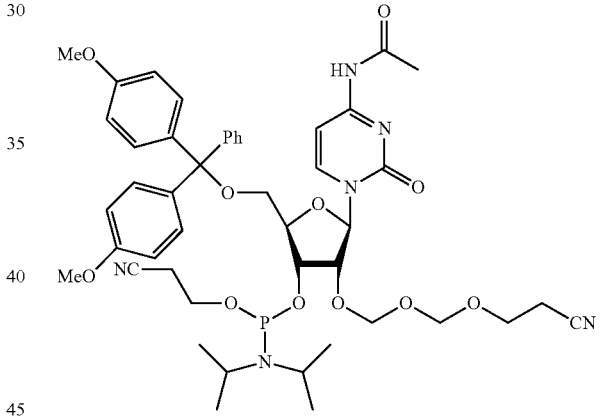

(A9)

[Chem. 29]

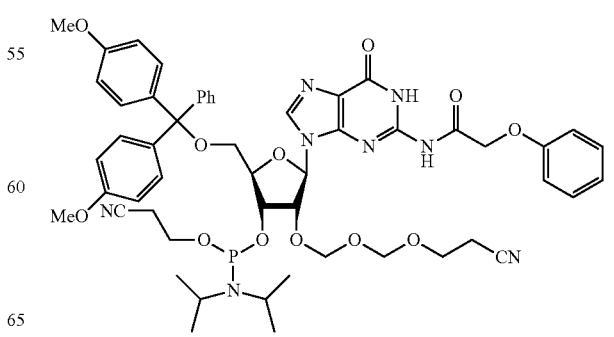

(A10)

Using a Controlled Pore Glass (CPG) as a solid support and a NTS M-4MX-E (manufactured by NIHON TECHNO SERVICE CO. LTD) as a nucleic acid synthesizer, according to a phosphoramidite solid phase synthesis method, an oligonucleotide composed by the above sequence (I) was synthesized from the 3' side to the 5' side. The synthesis was carried out on a scale of about 1 μmol scale when the NTS M-4MX-E (manufactured by NIHON TECHNO SERVICE CO. LTD) was used. Also in the synthesis, a uridine EMM amidite as described in Example 2 of US 2012/0035246, a cytidine EMM amidite as described in Example 3 thereof, an adenosine EMM amidite as described in Example 4 thereof, a guanosine EMM amidite as described in Example 5 thereof, and the compound (3) as described in WO 2017/188042 were used, and a high-purity solution of trichloro acetic acid in toluene was used as a deblocking solution, and 5-benzylmercapto-1H-tetrazole as a condensation agent, and iodine solution was used as an oxidation agent, and a phenoxy acetic anhydride solution and a N-methyl imidazole solution was used as a capping solution, -continued

[Chem. 30]

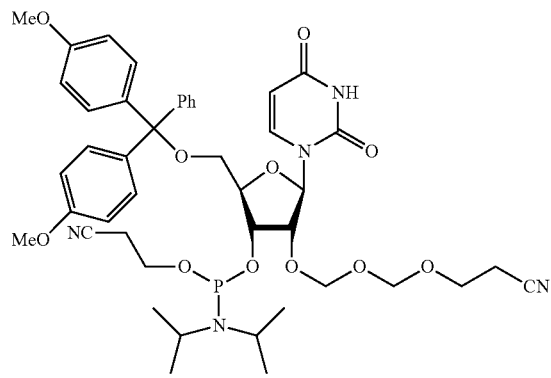

(A11)

Next, specific preparation examples of nucleic acid oligomer prepared by the process of the present invention are shown. Here, in the following examples, the oligonucleotides prepared according to the process of the present invention are nucleic acid oligomer having the above sequence Nos. 1 and 2.

Also, the guanosine derivatives as described in the following Examples and Comparative Examples represent the compounds represented by the following structural formula. A circle as depicted in the following structural formula represents CPG schematically.

[Chem.32]

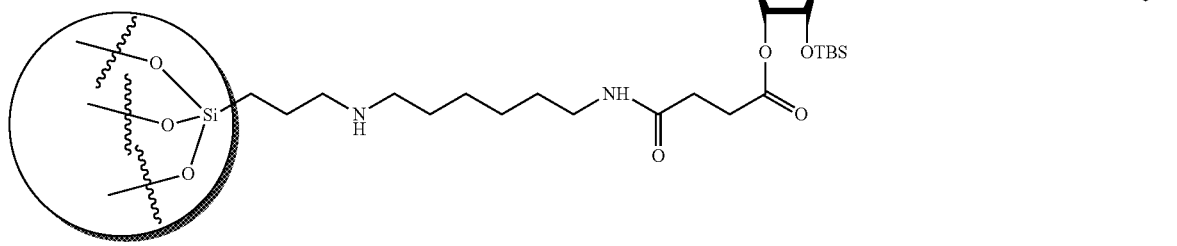

-continued

[Chem. 31]

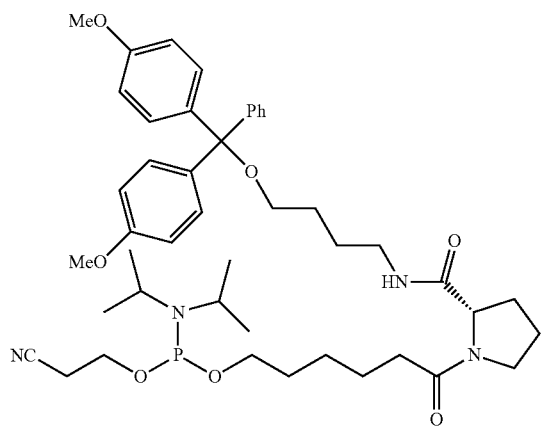

(A12)

Example 1

Using Controlled Pore Glass (CPG) on which 1.07 μmol guanosine derivative was supported, and each amidite represented by formula (A8), formula (A9), formula (A10) formula (A11), or formula (A12) respectively, the nucleic acid oligomer represented by sequence (I) was automatically synthesized by NTS M-4MX-E (manufactured by NIHON TECHNO SERVICE CO. LTD) from the 3'-side to the 5'-side. For procedures for automatic synthesis, firstly 3% trichloroacetic acid in toluene solution in 1.4 mL at each time was liquid-transferred to CPG, a trityl protecting group at 5' position was deprotected, and subsequently, 0.3 mL of each amidite, and 0.4 mL of 5-benzylmercapto-1H-tetrazole as a condensation agent were liquid-transferred to CPG, and a coupling reaction was proceeded on a hydroxyl group at 5'-position. Subsequently, after a solution of acetonitrile:water:pyridine=35.2:52.9:11.4 (% by weight) containing 17 mM iodine was stored at 60° C. for 161 hours, and shortly before synthesis, acetonitrile was added thereto to make a solution of acetonitrile:water:pyridine=58.2:34.2:7.4 (% by weight) containing 10 mM iodine, and 0.7 mL of the resulting solution was liquid-transferred, thereby a phosphite group was converted into a phosphate group. Successively, a 0.5 mL solution of 0.1 M phenoxy acetic anhydride and a 0.5 mL solution of 10% N-methyl imidazole/10% 2,6-lutidine in acetonitrile were used, thereby a capping reaction was carried out at the reaction point where the coupling reaction did not proceed. Further, these steps were repeated 52 times in total, thereby a nucleic acid oligonucleotide of a sequence represented by sequence (I) was synthesized on a CPG support, and a trityl protecting group at 5'-position was deprotected with a solution of 3% trichloroacetic acid in toluene. After that, a CPG support on which total amounts of oligonucleotide was supported was treated with 752 µL ammonia water and 252 µL ethanol to leave a nucleic acid oligomer from the solid support, and ammonia water and ethanol were removed by nitrogen-spraying. Next, the liberated oligonucleotide was solubilized in 400 µL dimethylsulfoxide, and after nitromethane 5.3 µL and a stir bar were added thereto, and a 530 µL (10.2 mole of TBAF per 1 mole of protecting group) of solution of 1M tetra-n-butyl ammonium fluoride (TBAF) in dimethyl sulfoxide, which was subjected to a dehydration treatment with molecular sieve 4A was inflowed thereto at 30° C. under stirring with a stirrer, and the resulting mixture was kept warm for 4 hours to deprotect a protecting group of 2'-EMM protecting group. The crude product was obtained by a precipitation operation. Yield was 8.6 mg and purity was 61%. For the obtained crude product, a purity of oligonucleotide was measured by using the method of the above measurement 1. Also, a yield of oligonucleotide was measured by using the method of the above measurement 2.

Example 2

Using Controlled Pore Glass (CPG) on which 1.02 µmol guanosine derivative was supported, and each amidite represented by formula (A8), formula (A9), formula (A10) formula (A11), or formula (A12) respectively, the nucleic acid oligomer represented by sequence (I) was automatically synthesized by NTS M-4MX-E (manufactured by NIHON TECHNO SERVICE CO. LTD) from the 3'-side to the 5'-side. For procedures for automatic synthesis, firstly 3% trichloroacetic acid in toluene solution in 1.4 mL at each time was liquid-transferred to CPG, a trityl protecting group at 5'-position was deprotected, and subsequently, 0.3 mL of each amidite, and 0.4 mL of 5-benzylmercapto-1H-tetrazole as a condensation agent were liquid-transferred to CPG, and a coupling reaction was proceeded on a hydroxyl group at 5'-position. Subsequently, after a solution of acetonitrile:water:pyridine=35.2:52.9:11.4 (% by weight) containing 17 mM iodine was stored at 60° C. for 24 hours, and shortly before synthesis, acetonitrile was added thereto to make a solution of acetonitrile:water:pyridine=58.2:34.2:7.4 (% by weight) containing 10 mM iodine, and 0.7 mL of the resulting solution was liquid-transferred, thereby a phosphite group was converted into a phosphate group. Successively, a 0.5 mL solution of 0.1 M phenoxy acetic anhydride and a 0.5 mL solution of 10% N-methyl imidazole/10% 2,6-lutidine in acetonitrile were used, thereby a capping reaction was carried out at the reaction point where the coupling reaction did not proceed. Further, these steps were repeated 52 times in total, thereby a nucleic acid oligonucleotide of a sequence represented by sequence (I) was synthesized on a CPG support, and a trityl protecting group at 5'-position was deprotected with a solution of 3% trichloroacetic acid in toluene. After that, a CPG support on which total amounts of oligonucleotide was supported was treated with 752 µL ammonia water and 252 µL ethanol to leave a nucleic acid oligomer from the solid support, and ammonia water and ethanol were removed by nitrogen-spraying. Next, the liberated oligonucleotide was solubilized in 400 µL dimethylsulfoxide, and after nitromethane 5.3 µL and a stir bar were added thereto, and a 530 µL (10.2 mole of TBAF per 1 mole of protecting group) of solution of 1M tetra-n-butyl ammonium fluoride (TBAF) in dimethyl sulfoxide, which was subjected to a dehydration treatment with molecular sieve 4A was inflowed thereto at 30° C. under stirring with a stirrer, and the resulting mixture was kept warm for 4 hours to deprotect a protecting group of 2'-EMM protecting group. The crude product was obtained by a precipitation operation. Yield was 7.3 mg and purity was 59%. For the obtained crude product, a purity of oligonucleotide was measured by using the method of the above measurement 1. Also, a yield of oligonucleotide was measured by using the method of the above measurement 2.

Example 3

Using Controlled Pore Glass (CPG) on which 1.03 µmol guanosine derivative was supported, and each amidite represented by formula (A8), formula (A9), formula (A10) formula (A11), or formula (A12) respectively, the nucleic acid oligomer represented by sequence (I) was automatically synthesized by NTS M-4MX-E (manufactured by NIHON TECHNO SERVICE CO. LTD) from the 3'-side to the 5'-side. For procedures for automatic synthesis, firstly 3% trichloroacetic acid in toluene solution in 1.4 mL at each time was liquid-transferred to CPG, a trityl protecting group at 5'-position was deprotected, and subsequently, 0.3 mL of each amidite, and 0.4 mL of 5-benzylmercapto-1H-tetrazole as a condensation agent were liquid-transferred to CPG, and a coupling reaction was proceeded on a hydroxyl group at 5' position. Subsequently, after a solution of acetonitrile:water:pyridine=35.2:52.9:11.4 (% by weight) containing 17 mM iodine was stored at 40° C. for 24 hours, and shortly before synthesis, acetonitrile was added thereto to make a solution of acetonitrile:water:pyridine=58.2:34.2:7.4 (% by weight) containing 10 mM iodine, and 0.7 mL of the resulting solution was liquid-transferred, thereby a phosphite group was converted into a phosphate group. Successively, a 0.5 mL solution of 0.1 M phenoxy acetic anhydride and a 0.5 mL solution of 10% N-methyl imidazole/10% 2,6-lutidine in acetonitrile were used, thereby a capping reaction was carried out at the reaction point where the coupling reaction did not proceed. Further, these steps were repeated 52 times in total, thereby a nucleic acid oligonucleotide of a sequence represented by sequence (I) was synthesized on a CPG support, and a trityl protecting group at 5'-position was deprotected with a solution of 3% trichloroacetic acid in toluene. After that, a CPG support on which total amounts of oligonucleotide was supported was treated with 752 µL ammonia water and 252 µL ethanol to leave a nucleic acid oligomer from the solid support, and ammonia water and ethanol were removed by nitrogen-spraying. Next, the liberated oligonucleotide was solubilized in 400 µL dimethylsulfoxide, and after nitromethane 5.3 µL and a stir bar were added thereto, and a 530 µL (10.2 mole of TBAF per 1 mole of protecting group) of solution of 1M tetra-n-butyl ammonium fluoride (TBAF) in dimethyl sulfoxide, which was subjected to a dehydration treatment with molecular sieve 4A was inflowed thereto at 30° C. under stirring with a stirrer, and the resulting mixture was kept warm for 4 hours to deprotect a protecting group of 2'-EMM protecting group.

The crude product was obtained by a precipitation operation. Yield was 8.1 mg and purity was 57%. For the obtained crude product, a purity of oligonucleotide was measured by using the method of the above measurement 1. Also, a yield of oligonucleotide was measured by using the method of the above measurement 2.

Reference Example 1

Using Controlled Pore Glass (CPG) on which 1.00 μmol guanosine derivative was supported, and each amidite represented by formula (A8), formula (A9), formula (A10) formula (A11), or formula (A12) respectively, the nucleic acid oligomer represented by sequence (I) was automatically synthesized by NTS M-4MX-E (manufactured by NIHON TECHNO SERVICE CO. LTD) from the 3'-side to the 5'-side. For procedures for automatic synthesis, firstly 3% trichloroacetic acid in toluene solution in 1.4 mL at each time was liquid-transferred to CPG, a trityl protecting group at 5'-position was deprotected, and subsequently, 0.3 mL of each amidite, and 0.4 mL of 5-benzylmercapto-1H-tetrazole as a condensation agent were liquid-transferred to CPG, and a coupling reaction was proceeded on a hydroxyl group at 5'-position. Subsequently, a solution of pyridine:water=88.7:10.0 (% by weight) containing 50 mM iodine was stored at 25° C. for 24 hours, and 0.7 mL of the resulting solution was liquid-transferred, thereby a phosphite group was converted into a phosphate group. Successively, a 0.5 mL solution of 0.1 M phenoxy acetic anhydride and a 0.5 mL solution of 10% N-methyl imidazole/10% 2,6-lutidine in acetonitrile were used, thereby a capping reaction was carried out at the reaction point where the coupling reaction did not proceed. Further, these steps were repeated 52 times in total, thereby a nucleic acid oligonucleotide of a sequence represented by sequence (I) was synthesized on a CPG support, and a trityl protecting group at 5'-position was deprotected with a solution of 3% trichloroacetic acid in toluene. After that, a CPG support on which total amounts of oligonucleotide was supported was treated with 752 μL ammonia water and 252 μL ethanol to leave a nucleic acid oligomer from the solid support, and ammonia water and ethanol were removed by nitrogen-spraying. Next, the liberated oligonucleotide was solubilized in 400 μL dimethylsulfoxide, and after nitromethane 5.3 μL and a stir bar were added thereto, and a 530 μL (10.2 mole of TBAF per 1 mole of protecting group) of solution of 1M tetra-n-butyl ammonium fluoride (TBAF) in dimethyl sulfoxide, which was subjected to a dehydration treatment with molecular sieve 4A was inflowed thereto at 30° C. under stirring with a stirrer, and the resulting mixture was kept warm for 4 hours to deprotect a protecting group of 2'-EMM protecting group. The crude product was obtained by a precipitation operation. Yield was 7.9 mg and purity was 42%. For the obtained crude product, a purity of oligonucleotide was measured by using the method of the above measurement 1. Also, a yield of oligonucleotide was measured by using the method of the above measurement 2.

Reference Example 2

Using Controlled Pore Glass (CPG) on which 1.04 μmol guanosine derivative was supported, and each amidite represented by formula (A8), formula (A9), formula (A10) formula (A11), or formula (A12) respectively, the nucleic acid oligomer represented by sequence (I) was automatically synthesized by NTS M-4MX-E (manufactured by NIHON TECHNO SERVICE CO. LTD) from the 3'-side to the 5'-side. For procedures for automatic synthesis, firstly 3% trichloroacetic acid in toluene solution in 1.4 mL at each time was liquid-transferred to CPG, a trityl protecting group at 5'-position was deprotected, and subsequently, 0.3 mL of each amidite, and 0.4 mL of 5-benzylmercapto-1H-tetrazole as a condensation agent were liquid-transferred to CPG, and a coupling reaction was proceeded on a hydroxyl group at 5'-position. Subsequently, a solution of acetonitrile:water:pyridine=58.2:34.4:7.2 (% by weight) containing 10 mM iodine was stored at 25° C. for 24 hours, and 0.7 mL of the resulting solution was liquid-transferred, thereby a phosphite group was converted into a phosphate group. Successively, a 0.5 mL solution of 0.1 M phenoxy acetic anhydride and a 0.5 mL solution of 10% N-methyl imidazole/10% 2,6-lutidine in acetonitrile were used, thereby a capping reaction was carried out at the reaction point where the coupling reaction did not proceed. Further, these steps were repeated 52 times in total, thereby a nucleic acid oligonucleotide of a sequence represented by sequence (I) was synthesized on a CPG support, and a trityl protecting group at 5'-position was deprotected with a solution of 3% trichloroacetic acid in toluene. After that, a CPG support on which total amounts of oligonucleotide was supported was treated with 752 μL ammonia water and 252 μL ethanol to leave a nucleic acid oligomer from the solid support, and ammonia water and ethanol were removed by nitrogen-spraying. Next, the liberated oligonucleotide was solubilized in 400 μL dimethylsulfoxide, and after nitromethane 5.3 μL and a stir bar were added thereto, and a 530 μL (10.2 mole of TBAF per 1 mole of protecting group) of solution of 1M tetra-n-butyl ammonium fluoride (TBAF) in dimethyl sulfoxide, which was subjected to a dehydration treatment with molecular sieve 4A was inflowed thereto at 30° C. under stirring with a stirrer, and the resulting mixture was kept warm for 4 hours to deprotect a protecting group of 2'-EMM protecting group. The crude product was obtained by a precipitation operation. Yield was 7.8 mg and purity was 35%. For the obtained crude product, a purity of oligonucleotide was measured by using the method of the above measurement 1. Also, a yield of oligonucleotide was measured by using the method of the above measurement 2.

Test results of Examples 1 to 3 and Reference Examples 1 to 2 are shown in Table 2.

TABLE 2

|  | Oxidation solution | | | | | Nucleic acid synthesis Nucleic acid purity (%) |
|---|---|---|---|---|---|---|
|  | Iodine ($I_2$) molar conc. (mM) | Pyridine (wt %) | Water (wt %) | Acetonitrile (wt %) | Temperature at storage and aging (° C.) | Period from a preparation to a nucleic acid synthesis |
| Example 1 | 10 | 7.4 | 34.1 | 58.2 | 60 | 161 hours | 61 |
| Example 2 | 10 | 7.4 | 34.1 | 58.2 | 60 | 24 hours | 59 |
| Example 3 | 10 | 7.4 | 34.1 | 58.2 | 40 | 24 hours | 57 |

TABLE 2-continued

| | Oxidation solution | | | | | Nucleic acid synthesis |
|---|---|---|---|---|---|---|
| | Iodine (I$_2$) molar conc. (mM) | Pyridine (wt %) | Water (wt %) | Acetonitrile (wt %) | Temperature at storage and aging (° C.) | Period from a preparation to a nucleic acid synthesis | Nucleic acid purity (%) |
| Reference Example 1 | 50 | 88.7 | 10.0 | 0.0 | 25 | 24 hours | 42 |
| Reference Example 2 | 10 | 7.2 | 34.3 | 58.2 | 25 | 24 hours | 35 |

From the above results of Table, comparing the case where the oxidation solution of the present invention that was subjected to a heat treatment at 40° C. or higher was used with the case of using the oxidation solutions of the Reference Examples 1 and 2, a nucleic acid oligomer with high purity could be obtained.

INDUSTRIAL APPLICABILITY

The present invention provides an efficient process for preparing nucleic acid oligomer. Also, an improvement in a purity of a nucleic acid oligomer that is prepared according to a process for preparing nucleic acid oligomer can be expected.

SEQUENCE LISTING FREE TEXT

Sequence Nos. 1 to 13 in a sequence listing represent a nucleotide sequence of oligonucleotide that is prepared according a process of the present invention.

The invention claimed is:

1. A process for preparing, by a phosphoramidite method, a nucleic acid compound having at its 5'-terminus a nucleotide represented by the following formula (I):

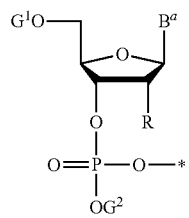
(I)

wherein
$G^1$ and $G^2$ each independently represent a protecting group for a hydroxy group, and $B^a$ represents a nucleic acid base which may be optionally protected with a protecting group,
R represents a protected hydroxy group, a hydrogen atom, a fluorine atom, a methoxy group, a 2-methoxyethyl group, or a OQ' group,
Q' represents a methylene group attached to a carbon atom at 4'-position of ribose, an ethylene group attached to a carbon atom at 4'-position of ribose, or an ethylidene group attached to a carbon atom at 4'-position of ribose, and
* represents a bond directing to 3' terminus side of a nucleic acid,
the process comprising:
reacting a precursor having a phosphite triester bond represented by the following formula (II):

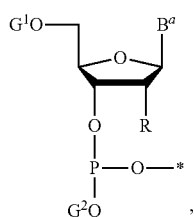
(II)

wherein
$G^1$, $G^2$, $B^a$, R and * are the same in the formula (I)
wherein the reacting the precursor having a phosphite triester bond is conducted in an oxidation solution which is at 40° C. or higher and comprises iodine, pyridine and water.

2. The process according to claim 1, wherein the precursor having a phosphite triester bond is a nucleic acid compound represented by the folllowing formula (4):

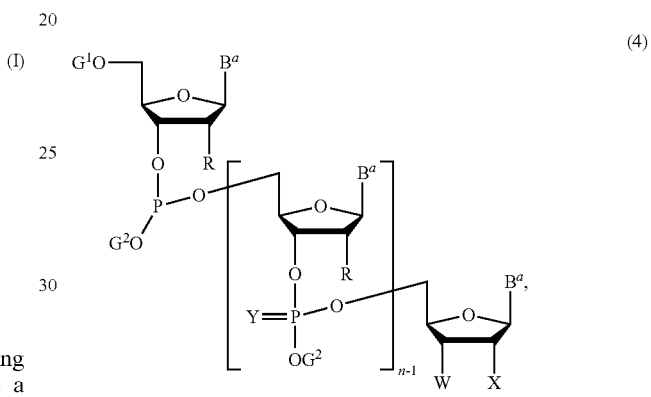
(4)

wherein
$G^1$ represents a protecting group for a hydroxy group,
$G^2$ is the same or different and each independently represents a protecting group for hydroxy group,
$B^a$ is the same or different and each independently represents a nucleic acid base which may be protected with a protecting group,
R is the same or different and each independently represents a protected hydroxy group, a hydrogen atom, a fluorine atom, a methoxy group, a 2-methoxyethyl group, or OQ' group,
Q' is the same or different and each independently represents a methylene group attached to a carbon atom at 4'-position of ribose, an ethylene group attached to a carbon atom at 4'-position of ribose, or an ethylidene group attached to a carbon atom at 4'-position of ribose,
Y is the same or different and each independently represents an oxygen atom or a sulfur atom,
n is an integer of from 1 to 200,
when X represents OZ, W represents OV, and V represents a protecting group for a hydroxy group,
when X represents R, W represents OZ,
Z represents a group having a structure comprising a solid support and a connecting group, and
when n is an integer of from 2 to 200, the nucleic acid compound represented by the formula (4) is optionally incorporated by a non-nucleotide linker instead of at least one nucleotide between nucleotides at 5' terminus and 3' terminus of the nucleic acid compound; and the compound containing a phosphate triester bond is a compound represented by the following formula (5):

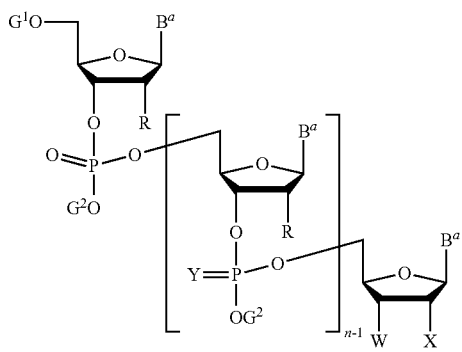

(5)

wherein $G^1$, $G^2$, $B^a$, R, n, W, X, and Y are the same as in the formula (4), a non-nucleotide linker is optionally incorporated instead of a nucleotide between nucleotides at 5' terminus and 3' terminus of the nucleic acid compound.

3. The process for preparing nucleic acid oligomer according to claim 2, further comprising elongating a chain of a nucleic acid compound represented by the formula (5) to any chain length by an amidite method to obtain a nucleic acid represented by the following formula (5'):

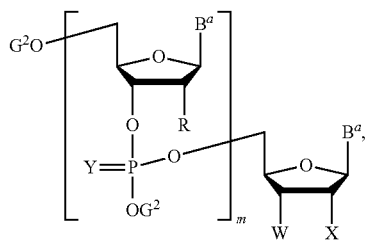

(5')

wherein $G^2$, $B^a$, R, X and W are the same as in the formula (5), $G^5$ represents a protecting group for a hydroxy group, or a hydrogen atom, m is an integer satisfying m≥n, Y is the same or different and each independently represents an oxygen atom or a sulfur atom, with the proviso that at least one of Y is an oxygen atom, cutting out the compound represented by the following formula (6) from the compound represented by the formula (5'):

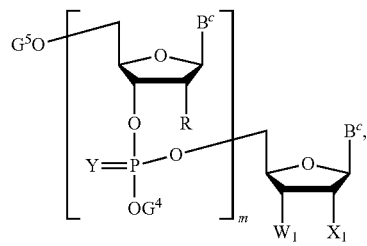

(6)

wherein $G^5$, R and m are the same as in the formula (5'), $B^c$ is the same or different and each independently represents a nucleic acid base, $G^4$ represents a hydrogen atom, an alkali metal ion, an ammonium ion, an alkyl ammonium ion, or a hydroxyl alkyl ammonium ion, Y each independently represents an oxygen atom or a sulfur atom, wherein at least one Y is an oxygen atom, and $X_1$ represents a hydroxy group, and $W_1$ represents OV, wherein V represents a protecting group for a hydroxy group, or $X_1$ represents R and $W_1$ represents a hydroxy group, from the compound represented by the formula (5'), deprotecting the compound represented by the formula (6) to prepare a deprotected nucleic acid oligomer represented by the following formula (7):

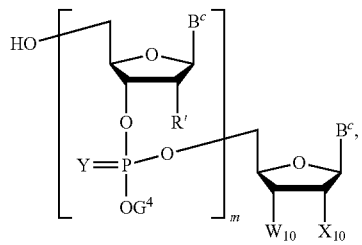

(7)

wherein m, Y, $G^4$, and $B^c$ are the same as in the formula (6),

R' is the same or different and each independently represents a hydroxy group, a hydrogen atom, a fluorine atom, a methoxy group, a 2-methoxyethyl group, or a OQ' group, Q' is the same or different and each independently represents a methylene group attached to a carbon atom at 4'-position of ribose, an ethylene group attached to a carbon atom at 4'-position of ribose, or an ethylidene group attached to a carbon atom at 4'-position of ribose, $X_{10}$ and $W_{10}$ each independently represent a hydroxy group, or $X_{10}$ represents R', and $W_{10}$ represents a hydroxy group.

4. The process according to claim 2, wherein the non-nucleotide linker comprises an amino acid backbone.

5. The process according to claim 4, wherein the non-nucleotide linker comprising an amino acid backbone has a structure selected from the group consisting of the following formulae (A14-1), (A14-2) and (A14-3)

(A14-1)

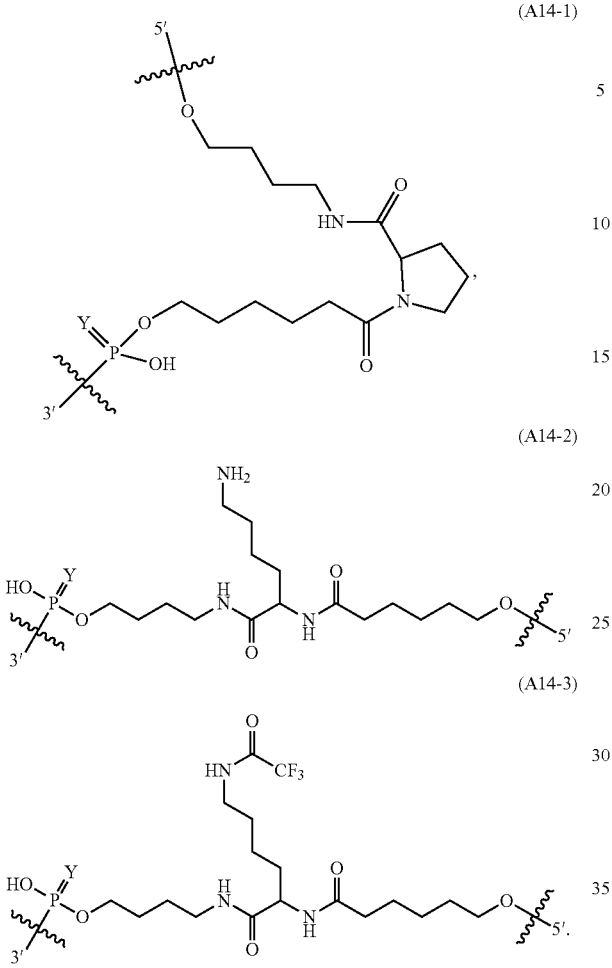

(A14-2)

(A14-3)

6. The process according to claim 1, wherein the oxidation solution comprises iodine at a concentration of from 0.005 M to 2 M.

7. The process according to claim 1, wherein a concentration of iodine in an oxidation solution is from 0.005 M to 0.2 M.

8. The process according to claim 1, wherein a concentration of iodine in an oxidation solution is from 0.007 M to 0.1 M.

9. The process according to claim 1, wherein a concentration of iodine in an oxidation solution is from 0.008 M to 0.07 M.

10. The process according to claim 1, further comprising: preparing the oxidation solution by mixing iodine, pyridine and water.

11. The process according to claim 10, wherein the oxidation solution comprises at least one solvent selected from the group consisting of acetonitrile and tetrahydrofuran.

12. The process according to claim 10, wherein the oxidation solution further comprises acetonitrile solvent.

13. The process according to claim 11, wherein the solvent of the oxidation solution is a mixture of solvents which is obtained by mixing pyridine, water, acetonitrile, and tetrahydrofuran in a volume ratio of 1 to 90:1 to 50:0 to 90:0 to 90.

14. The process according to claim 11, wherein a solvent of the oxidation solution is a mixture of solvents which is obtained by mixing pyridine, water and acetonitrile in a volume ratio of 1 to 90:1 to 50:0 to 90.

15. The process according to claim 1, further comprising: aging the oxidation solution in storage at a temperature of from 40° to 60° before use in the reaction of the precursor having a phosphite triester.

16. The process according to claim 1, wherein the nucleic acid compound comprises a ribonucleoside (RNA).

17. The process according to claim 2, wherein the nucleic acid compound is ribonucleoside (RNA), and which has 2' protecting group is a protecting group represented by the following formula (12):

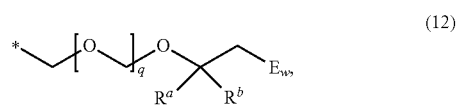

(12)

wherein q is an integer of from 1 to 5, $R^a$ and $R^b$ are the same or different and each independently represent a methyl group, an ethyl group, or a hydrogen atom,

* represents an oxygen atom of OQ group, and $E_w$ group represents an electron-attracting group.

18. The process according to claim 17, wherein $R^a$ and $R^b$ are both simultaneously a hydrogen atom, and $E_w$ represents a cyano group.

19. The process according to claim 1, wherein the nucleic acid compound is a ribonucleoside (RNA) comprising at least 40 nucleotides in a chain.

20. The process according to claim 1, further comprising: preparing the oxidation solution.

21. The process according to claim 1, wherein $G^1$ represents the following group:

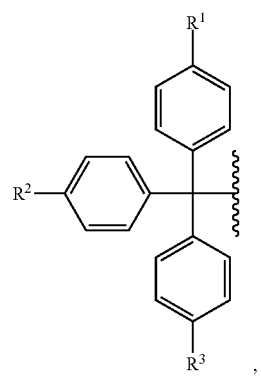

wherein $R^1$, $R^2$ and $R^3$ are the same or different and each independently represent a hydrogen atom or an alkoxy group.

22. The process according to claim 2, wherein the solid support comprises an inorganic porous support.

23. The process according to claim 1, wherein when R is a protected hydroxy group, the protecting group of the protected hydroxy group is selected from the group consisting of a 2'-tertbutyldimethylsilyl (TBDMS) group, a 2'-bis (2-acetoxy) methyl (ACE) group, a 2'-(triisopropylsilyloxy) methyl (TOM) group, a 2'-(2-cyanoethoxy) ethyl (CEE) group, a 2'-(2-cyanoethoxy)methyl (CEM) group, and a 2'-para-toluylsulfonylethoxymethyl (TEM) group.

\* \* \* \* \*

```
                      SEQUENCE LISTING

<160> NUMBER OF SEQ ID NOS: 13

<210> SEQ ID NO 1
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 1
agcagaguac acacagcaua uacc                                          24

<210> SEQ ID NO 2
<211> LENGTH: 26
<212> TYPE: RNA
<213> ORGANISM: Artificial Sequence
<220> FEATURE:
<223> OTHER INFORMATION: Synthetic oligonucleotide

<400> SEQUENCE: 2
gguauaugcu guguguacuc ugcuuc                                        26

<210> SEQ ID NO 3
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(7), (17)..(17)
<223> OTHER INFORMATION: um
<220> FEATURE:
<221> NAME/KEY: modified_base
<222> LOCATION: (20)..(21)
<223> OTHER INFORMATION: dT

<400> SEQUENCE: 3
auggaanacu cuuggunacn n                                             21
```

```
<210> SEQ ID NO 4
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(2), (12)..(12), (14)..(15), (19)..(19)
<223> OTHER INFORMATION: um
<220> FEATURE:
<221> NAME/KEY: modified_base
<222> LOCATION: (5)..(6), (16)..(17)
<223> OTHER INFORMATION: cm
<220> FEATURE:
<221> NAME/KEY: modified_base
<222> LOCATION: (20)..(21)
<223> OTHER INFORMATION: dT

<400> SEQUENCE: 4
gnaannaaga gnannnnann n                                             21

<210> SEQ ID NO 5
<211> LENGTH: 36
<212> TYPE: RNA
<213> ORGANISM: Artificial Sequence
<220> FEATURE:
<223> OTHER INFORMATION: Synthetic oligonucleotide

<400> SEQUENCE: 5
agagccagcc uucuuauugu uuuagagcua ugcugu                             36

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 6
ccaugagaag uaugacaaca gcc                                           23

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 7
ggcuguuguc auacuucuca ugguu                                         25

<210> SEQ ID NO 8
<211> LENGTH: 67
<212> TYPE: DNA
<213> ORGANISM: Artificial Sequence
<220> FEATURE:
<223> OTHER INFORMATION: Synthetic oligonucleotide

<400> SEQUENCE: 8
acagcauagc aaguuaaaau aaggcuaguc cguuaucaac uugaaaaagu ggcaccgagu   60
cggugcu                                                             67

<210> SEQ ID NO 9
<211> LENGTH: 94
<212> TYPE: DNA
<213> ORGANISM: Artificial Sequence
<220> FEATURE:
```

```
<223> OTHER INFORMATION: Synthetic oligonucleotide

<400> SEQUENCE: 9 guuuuccuu uucaaagaaa ucuccugggc accuaucuuc uuaggugccc ucccuuguuu      60
aaaccugacc aguuaaccgg cugguuaggu uuuu                                94

<210> SEQ ID NO 10
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 10
aguccucauc ucccucaagc guuuagagc uaguaauagc aaguuaaaau aaggcuaguc      60
cguuaucaac uugaaaaagu ggcaccgagu cggugcuuuu                         100

<210> SEQ ID NO 11
<211> LENGTH: 113
<212> TYPE: DNA
<213> ORGANISM: Artificial Sequence
<220> FEATURE:
<223> OTHER INFORMATION: Synthetic oligonucleotide

<400> SEQUENCE: 11
gcagauguag uguuuccaca guuuaagagc uaugcuggaa acagcauagc aaguuuaaau     60
aaggcuaguc cguuaucaac uugaaaaagu ggcaccgagu cggugcuuuu uuu           113

<210> SEQ ID NO 12
<211> LENGTH: 113
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1), (8)..(8), (17)..(18)
<223> OTHER INFORMATION: dA
<220> FEATURE:
<221> NAME/KEY: modified_base
<222> LOCATION: (2)..(2), (19)..(19)
<223> OTHER INFORMATION: dG
<220> FEATURE:
<221> NAME/KEY: modified_base
<222> LOCATION: (3)..(3), (6)..(6), (9)..(9), (11)..(11), (15)..(15)
<223> OTHER INFORMATION: dT
<220> FEATURE:
<221> NAME/KEY: modified_base
<222> LOCATION: (4)..(5), (7)..(7), (10)..(10), (12)..(14), (16)..(16),
      (20)..(20)
<223> OTHER INFORMATION: dC

<400> SEQUENCE: 12
nnnnnnnnnn nnnnnnnnnn guuuaagagc uaugcuggua acagcauagc aaguuuaaau     60
aaggcuaguc cguuaucaac uugaaaaagu ggcaccgagu cggugcuuuu uuu           113

<210> SEQ ID NO 13
<211> LENGTH: 113
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: am
<220> FEATURE:
```

```
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3), (110)..(113)
<223> OTHER INFORMATION: um

<400> SEQUENCE: 13
nnnccucauc ucccucaagc guuuaagagc uaugcuggua acagcauagc aaguuuaaau      60
aaggcuaguc cguuaucaac uugaaaaagu ggcaccgagu cggugcuuun nnu            113
```